US008404158B2

(12) United States Patent
Curtis et al.

(10) Patent No.: US 8,404,158 B2
(45) Date of Patent: *Mar. 26, 2013

(54) SYSTEM AND METHOD FOR LIQUID DELIVERY EVALUATION USING SOLUTIONS WITH MULTIPLE LIGHT ABSORBANCE SPECTRAL FEATURES

(75) Inventors: Richard H. Curtis, Gorham, ME (US); Ceara McNally, Poland, ME (US); Charles A. Ewing, Westbrook, ME (US); John Thomas Bradshaw, Gorham, ME (US)

(73) Assignee: Artel, Inc., Westbrook, ME (US)

( * ) Notice: Subject to any disclaimer, the term of this patent is extended or adjusted under 35 U.S.C. 154(b) by 1143 days.

This patent is subject to a terminal disclaimer.

(21) Appl. No.: 12/098,864

(22) Filed: Apr. 7, 2008

(65) Prior Publication Data

US 2009/0250664 A1 Oct. 8, 2009

(51) Int. Cl.
*G01N 33/00* (2006.01)
*G01N 21/00* (2006.01)
(52) U.S. Cl. .................................. 252/408.1; 356/436
(58) Field of Classification Search ............... 252/408.1; 356/436
See application file for complete search history.

(56) References Cited

U.S. PATENT DOCUMENTS

| | | | |
|---|---|---|---|
| 3,492,095 A | 1/1970 | Tillem | |
| 3,565,537 A | 2/1971 | Fielding | |
| 3,705,000 A | 12/1972 | Guerra | |
| 3,737,237 A | 6/1973 | Zurasky | |
| 3,869,211 A | 3/1975 | Watanabe et al. | |
| 3,920,580 A | 11/1975 | Mast | |
| 4,128,339 A | 12/1978 | Yamazaki et al. | |
| 4,248,536 A | 2/1981 | Hijikata | |
| 4,305,659 A | 12/1981 | Bilstad et al. | |
| 4,354,376 A | 10/1982 | Greenfield et al. | |

(Continued)

FOREIGN PATENT DOCUMENTS

EP 0431578 B1 6/1991

OTHER PUBLICATIONS

Cohn et al., "Precision Techniques for Measuring Liquid Quantity," Control Engineering, vol. 15, Jan. 1968, U.S., pp. 51-55 (5 pages).

(Continued)

*Primary Examiner* — Kevin Joyner
(74) *Attorney, Agent, or Firm* — Verrill Dana, LLP; Chris A. Caseiro

(57) ABSTRACT

A system and related method for improved liquid delivery evaluation using a solution containing one or more dyes such that the solution exhibits multiple distinct detectable light absorbance spectral features for calibrating or testing over extended volume or dilution ranges are described. The system includes: a photometric instrument capable of measuring optical absorbance at multiple wavelengths; one or more sample solutions to be dispensed using the liquid delivery system whose performance is being tested or calibrated; and vessels optionally pre-filled, or filled by the user, with diluent solution. The sample solutions contain one or more dyes, chosen so that multiple distinct detectable light absorbance spectral features, such as peaks and/or valleys and/or plateaus of the solution can be distinguished for volume or dilution ranges of interest. The concentrations of the dyes may be chosen so that a large volume delivery device is calibrated using a spectral feature in the solution with a low absorbance per unit pathlength, while a small volume delivery device is calibrated with the same sample solution but using a different spectral feature with a high absorbance per unit pathlength.

7 Claims, 6 Drawing Sheets

U.S. PATENT DOCUMENTS

| | | | |
|---|---|---|---|
| 4,357,105 | A | 11/1982 | Liretz |
| 4,405,235 | A | 9/1983 | Rossiter |
| 4,582,684 | A | 4/1986 | Vogel et al. |
| 4,595,561 | A | 6/1986 | Thornton et al. |
| 4,805,623 | A | 2/1989 | Jobsis |
| 5,064,282 | A | 11/1991 | Curtis |
| 5,092,677 | A | 3/1992 | Curtis |
| 5,125,747 | A | 6/1992 | Sayegh et al. |
| 5,244,813 | A | 9/1993 | Walt et al. |
| 5,258,308 | A | 11/1993 | Freeman et al. |
| 5,298,978 | A * | 3/1994 | Curtis et al. .................. 356/627 |
| 5,492,673 | A | 2/1996 | Curtis et al. |
| 5,637,505 | A * | 6/1997 | Li et al. .............. 436/8 |
| 5,766,875 | A | 6/1998 | Hafeman et al. |
| 5,959,738 | A | 9/1999 | Hafeman et al. |
| 5,963,318 | A | 10/1999 | Held |
| 6,188,476 | B1 | 2/2001 | Hafeman et al. |
| 6,320,662 | B1 | 11/2001 | Hafeman et al. |
| 6,339,472 | B1 | 1/2002 | Hafeman et al. |
| 6,661,512 | B2 | 12/2003 | Fernando et al. |
| 6,741,365 | B2 | 5/2004 | Curtis |
| 2002/0149772 | A1 | 10/2002 | Halg |
| 2004/0246501 | A1 | 12/2004 | Curtis et al. |
| 2005/0168737 | A1 | 8/2005 | Bradshaw et al. |
| 2007/0141709 | A1 * | 6/2007 | Albert et al. ...................... 436/8 |
| 2007/0161114 | A1 | 7/2007 | Curtis et al. |
| 2008/0070317 | A1 | 3/2008 | Bradshaw et al. |

OTHER PUBLICATIONS

Waring et al., "The Chemistry and Application of Dyes," 1990, Plenum Press, New York, U.S., p. 282 (2 pages).

Lubs, "The Chemistry of Synthetic Dyes and Pigments," Amer. Chem. Soc., Color and Chemical Constitution of Dyes, 1970, Hafner Publishing, Darien, CT, US, pp. 675-676 (3 pgs).

International Standard, ISO 8655-7, "Piston-operated volumetric apparatus—Part 7: Non-gravimetric methods for the assessment of equipment performance," Sep. 1, 2005, (27 pgs).

Taylor et al., "A Standard Operating Procedure for Assessing Liquid Handler Performance in High-Throughput Screening", Journal of Biomolecular Screening 7:554-569 (2002).

International Search Report and Written Opinion in corresponding PCT application, International Searching Authority/ US, Jun. 2, 2009, 7 pp.

International Search Report and Written Opinion in PCT application No. PCT/US2009/002089 for related invention, May 18, 2011, 15 pp.

* cited by examiner

SYSTEM AND METHOD FOR LIQUID DELIVERY EVALUATION USING SOLUTIONS WITH MULTIPLE LIGHT ABSORBANCE SPECTRAL FEATURES

CROSS REFERENCE TO RELATED APPLICATION

The present invention is related to application Ser. No. 12/098,875, filed on the same date hereof, with the same title and assigned to a common assignee, now U.S. Pat. No. 7,791,716. The content of that related patent is incorporated herein by reference.

BACKGROUND OF THE INVENTION

1. Field of the Invention

The present invention relates to a system for determining the volume of a liquid delivery. More particularly, the present invention relates to systems and related methods to test or calibrate liquid delivery devices using a sample solution having multiple distinct detectable light absorbance spectral features using one or more dyes to cover a volume range, or a dilution range, of interest.

2. Description of the Prior Art

All currently manufactured calorimetric systems for testing or calibrating liquid delivery devices (e.g., the PCS® system and the MVS® system, both offered by Artel, Inc. of Westbrook, Me., assignee of the present invention and application, and the Pipette Volume Calibration Kit offered by VistaLab of Mt. Kisco, N.Y.) use a multiplicity of sample solutions for the purpose of testing a wide range of deliverable solution volumes. The sample solution is delivered by the device being tested into a diluent in a measurement vessel, and the solutions are mixed before measuring the absorbance of the resulting mixture. A concentrated sample solution is used to test a small liquid delivery volume, and a more dilute sample solution is used to test a large liquid delivery volume. As used herein, a "vessel" is any vial, cell, bottle, microtiter plate or other type of container for retaining a fluid therein, whether such vessel is sealed or not. Also, the vessel may be designed for collecting optical absorbance measurements by use of a horizontal beam spectrophotometer (such as a conventional UV-Vis spectrophotometer like the Cary 5000, Varian, Inc., Palo Alto, Calif.) or a vertical beam spectrophotometer (such as a microtiter plate reader like the ELx800, BioTek Instruments, Winooski, Vt.).

In simplified terms, the PCS® system includes one or more devices and one or more solutions used to calibrate a single-channel liquid dispensing device. On the other hand, the MVS® system includes one or more devices and one or more solutions used to calibrate a multi-channel liquid dispensing device. The difference between the two systems relates to the calculations performed subsequent to conducting absorbance measurements at one or more wavelengths corresponding to features present in the spectrum of the solution(s).

In the case of one commercial embodiment of the Artel PCS® system, for example, four different concentrations of a sample solution, each targeting the same spectral feature, are provided to cover the volume range from 2 microliters (µl) to 5000 µl. Two additional concentrations of the same sample solution extend the range down to 0.1 µl. The reason for using different concentrations is to maintain a measurable signal level (absorbance change resulting from the delivery of an aliquot of sample solution or diluent) within a defined signal range over the full range of liquid delivery volumes. That is to say, each concentration of sample solution is manufactured to produce a final measurable absorbance within a defined absorbance range for any delivered volume that is within the volume range for which the solution is designed. All concentrations of sample solution of the PCS® system are designed to produce measurable absorbance values over the same absorbance range. The disadvantage to using a multiplicity of solutions is that the user needs to stock them, rotate stock to make sure that the solutions are within their expiration date, and then choose which one or ones to use, and to dispense the correct solution(s) into one or more vessels from which the delivery device can aspirate the correct solution. There is ample opportunity for error, waste of unused solutions from the vessels, and waste of time and unnecessary distraction from the job of testing the delivery device. It is thus desirable to devise a method that would reduce the number of sample solutions required to test the entire volume range that can be delivered by a liquid delivery device.

In addition to volume delivery testing, colorimetric measurement systems using multiple concentrations of the same sample solution can be used to test dilution protocols, which are commonly employed in life science laboratories. Such dilution protocols are often employed in drug discovery testing where a compound of interest is serially diluted across a microtiter plate. For example, the user dispenses 200 µL of sample solution into the first column of a microtiter plate and then aspirates 100 µL from that first column and dispenses it into 100 µL of diluent in the second column, creating a 1:2 dilution ratio of the sample solution in the second column. Serially repeating this process across all columns in the plate results in a range of dilutions from a 1:1 ratio up to a 1:2048 ratio. An effective dilution protocol system is described in pending U.S. patent application Ser. No. 11/854,594, filed Sep. 13, 2007, having as assignee the assignee of the present application. The entire content of the referenced Ser. No. 11/854,594 pending application is incorporated herein by reference. If the MVS® system were used to test the dilutions made in this example, five sample solutions would be needed to cover the entire range of dilution ratios because each sample solution can only test a four- or five-fold range of dilution ratios before the absorbance signal of the single spectral feature in the sample solution is too low to be measured by the microtiter plate reader. Thus, to measure all dilution steps of this process, the serial dilution protocol has to be repeated for each of the five sample solutions such that a limited range of the dilution ratio series is tested with each sample solution. That is to say, each of the five sample solutions is serially diluted using the defined protocol. For each of the sample solutions, only a portion of the produced dilutions will be within a measurable absorbance range, but the combination of data from all sample solutions will provide measurements for every step of the entire process. As a result, many test vessels are filled with sample solution to cover the entire dilution range of interest but only a fraction are actually used. Thus, there is a waste of solution and of time.

Alternative methods for testing serial dilution protocols include fluorescence, which covers a far greater range (1,000-10,000 fold greater range) of dilution ratios before the signal is too low to measure. However, the fluorescence method introduces variability because of the instability of fluorescent dyes due to photo-bleaching, quenching, etc, and also lacks the traceability to international standards of an absorbance-based photometric approach. Therefore, it is also desirable to devise an absorbance-based photometric method that would measure an extended range of dilution ratios using one sample solution containing multiple spectral features, each capable of testing a unique four or five fold range of dilution ratios as an alternative to fluorimetry testing of dilution processing as noted herein.

Other systems have been described for enhancing calibration accuracy. See, for example, U.S. Pat. No. 5,298,978 for "Pipette Calibration System" of Curtis et al., incorporated herein by reference, U.S. Pat. No. 4,354,376 for "Kit for Calibrating Pipettes" of Greenfield, and U.S. Pat. Nos. 6,741,365 and 7,187,455 for "Photometric Calibration of Liquid Volumes" of Curtis, also incorporated herein by reference. These systems have limitations resolved by the use in the present invention of a dye, or a plurality of dyes, capable of producing multiple distinct detectable light absorbance spectral features in a smaller set of sample solutions, wherein each distinct detectable light absorbance spectral feature allows calibration or testing over a specific volume range. A dye is any molecule or chemical compound that imparts one or more features to the absorbance spectrum of the solution. This definition is not intended to limit the feature to the visible region of the spectrum, nor to limit the spectral feature to the dye or dyes alone. The solvent could also impart a spectral feature that could be used as is described in this invention. One skilled in the art may recognize that a dye may be the functional equivalent of a chromophore. As used herein, "distinct detectable light absorbance spectral features" are distinct and detectable peaks, valleys, plateaus, or any combination of peaks and valleys and plateaus in the absorbance spectrum of a solution under test. In the case of U.S. Pat. No. 4,354,376 of Greenfield, there is only one distinct detectable light absorbance spectral feature. In the case of U.S. Pat. No. 5,298,978 of Curtis et al., there is a second feature present in the spectrum of the diluent solely for the purpose of determining the pathlength of light through the vessel before any sample solution is added to the vessel, minimizing uncertainty in the results due to uncertainty in vessel dimensions. This second spectral feature is not contained in the sample solution dispensed with the liquid delivery device under test. In the case of U.S. Pat. Nos. 6,741,365 and 7,187,455 to Curtis, two spectral features are used to eliminate uncertainty in results that would otherwise occur due to uncertainty in the volume of diluent added to the tapered wells of the microtiter plate used as a measurement vessel. Both spectral features are contained in the sample solutions, however the function of the second spectral feature (in that particular case, $CuCl_2$) is to correct for the unknown volume of diluent, not to cover a wider range of dispensing volumes.

What is needed is a system and related method to resolve the limitations of the existing liquid delivery measurement systems in which the use of colorimetric techniques to evaluate liquid delivery devices or protocols requires the use of an excess number of sample solutions for volume and dilution ranges of interest.

SUMMARY OF THE INVENTION

The purpose of the present invention is to resolve the above-noted limitations by simplifying the testing or calibrating of liquid delivery devices. This greater simplicity will reduce costs, allow users to do their work more effectively, and reduce the likelihood of errors. This invention achieves this greater simplicity by reducing the number of different sample solutions required to test a large range of volumes, or a large range of dilutions, to a minimal number, ideally only one, from typically four. The present invention is designed to be in conformance with International Standards Organization (ISO) standard 8655 part 7 and, further, it is designed to provide results traceable to international standards, thereby making it advantageous over fluorimetric techniques. Finally, this invention is designed to extend the testable dilution range or volume range of a sample solution by increasing the number of spectral features in the sample solution. Specifically, an extended testable volume range enables the use of a single sample solution, optimally, to cover pipettes (or other relevant delivery devices) most commonly tested or calibrated in the volume range of about 2 µl to about 5000 µl. Similarly, an extended range of dilutions can be tested using a single sample solution, optimally, for a range of 1:1 up to 1:2500. In the event a single sample solution cannot be used for a desired volume or dilution range, the present invention nevertheless enables use of a smaller set of sample solutions than has heretofore been required.

The present invention is a system and related method for improved liquid delivery evaluations using solutions containing one or more dyes or other light absorbing compounds or chemicals, which in combination or individually, exhibit multiple distinct detectable light absorbance spectral features, each solution capable of calibrating or testing over a wide volume range, or dilution range, of interest. The system includes: a photometric instrument capable of measuring optical absorbance at multiple wavelengths; one or more reagents including one or more sample solutions to be dispensed using the liquid delivery system whose performance is being tested or calibrated; and, optionally, vessels pre-filled with diluent solution. The sample solution contains at least one dye, chosen so that when any volume within a volume range of interest is dispensed into a vessel, a distinct detectable light absorbance spectral feature exists at a wavelength and absorbance level within the dynamic range of the photometric instrument. In a solution containing multiple dyes, for example, the concentrations of the different dyes are chosen so that a relatively large volume delivered by a liquid delivery device is calibrated using a spectral feature in the solution with a low absorbance per unit pathlength, while a relatively small volume delivery is calibrated with the same sample solution but using a different spectral feature with a high absorbance per unit pathlength.

The use of a minimal number of sample solutions suitable to calibrate or test over an extended volume range, or over an extended dilution range, due to the multiple distinct detectable light absorbance spectral features, provides a simpler user protocol with less chance for user error and greater convenience. This resolves a problem noted in regard to at least one of the systems of the prior references, in which four different concentrations of sample solution are used to cover an extended volume or dilution range commonly delivered by various pipette sizes. This also resolves a problem noted for the MVS® system in which a substantial number of different concentrations of sample solution must be used to cover an extended dilution range of 1:1 up to 1:2048.

As noted, the purpose of putting one or more dyes providing multiple distinct detectable light absorbance spectral features into a minimal number of sample solutions is to simplify operation of the system. Specifically, the operator does not need to choose a corresponding concentration of dye in a solution for each delivery volume range, or dilution range, of interest, since a lesser number of solutions serves the entire range of delivery volumes or dilution ratios. The system can use either a vertical beam photometer or a horizontal beam photometer, and can use either a fixed or a removable measurement vessel. The diluent can contain a dye or not. The system can be configured to test or calibrate a single delivery at a time or multiple deliveries at once as is the case with a multi-channel delivery device.

DETAILED DESCRIPTION OF A PREFERRED EMBODIMENT OF THE INVENTION

Figure 1:
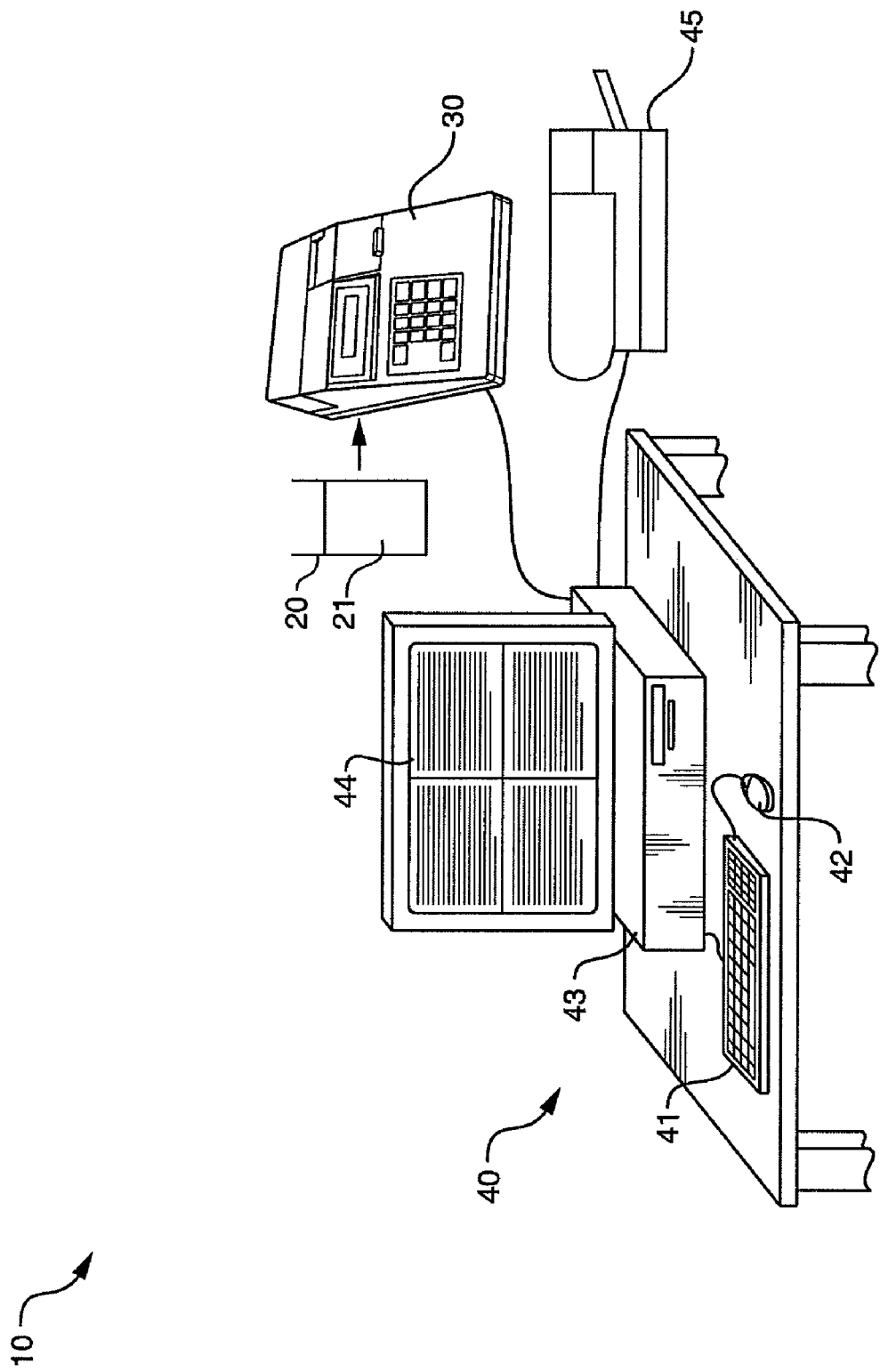
FIG. 1 is a simplified representation of an embodiment of a set of devices that may be used to carry out the method of the present invention, including a spectrophotometer and a computing system.

An embodiment of a set of devices associated with a system suitable for conducting the steps of the methods of the present invention is shown in FIG. 1. It is to be understood that other devices performing the same functions may be employed without deviating from the intended functions of the devices represented in FIG. 1, in which a volume determining apparatus 10 includes as primary components a liquid holder 20, a spectrophotometer 30, and a computing system 40 capable of carrying out calculations defined through computer-executable software and/or firmware, which software or firmware may be associated with the computing system 40 or alternatively with a liquid dispenser such as the type shown in FIG. 2. It is to be understood that the computing system 40 and associated programming may reside in other devices of the system including, for example, the spectrophotometer 30. Further, any one or more of the example devices described herein may be integrated into a single device without deviating from the primary aspects of the invention.

The liquid holder 20 is a vessel that may be used to retain liquid 21 to be analyzed. The liquid holder 20 may be placed into the spectrophotometer 30. The spectrophotometer 30 is capable of being instructed to initiate absorbance measurements on the liquid 21 in the liquid holder 20. These instructions may be carried out through one or more input devices of the spectrophotometer 30 or through the computing system 40. The computing system 40 includes one or more input devices, such as a keyboard 41, a mouse 42, or a combination thereof, which may be used to control the spectrophotometer 30 and/or to perform calculations of volume determination based on the absorbance measurements. The computing system 40, including a computer processor 43 and memory storage, is configured to carry out executable-system instructions for volume determination. Input information and output information may be viewed on a computer display 44. Optionally, a local or remote printer 45 may be employed to print out input information and/or output information, or the information may simply be observed on the display 44.

Figure 2:
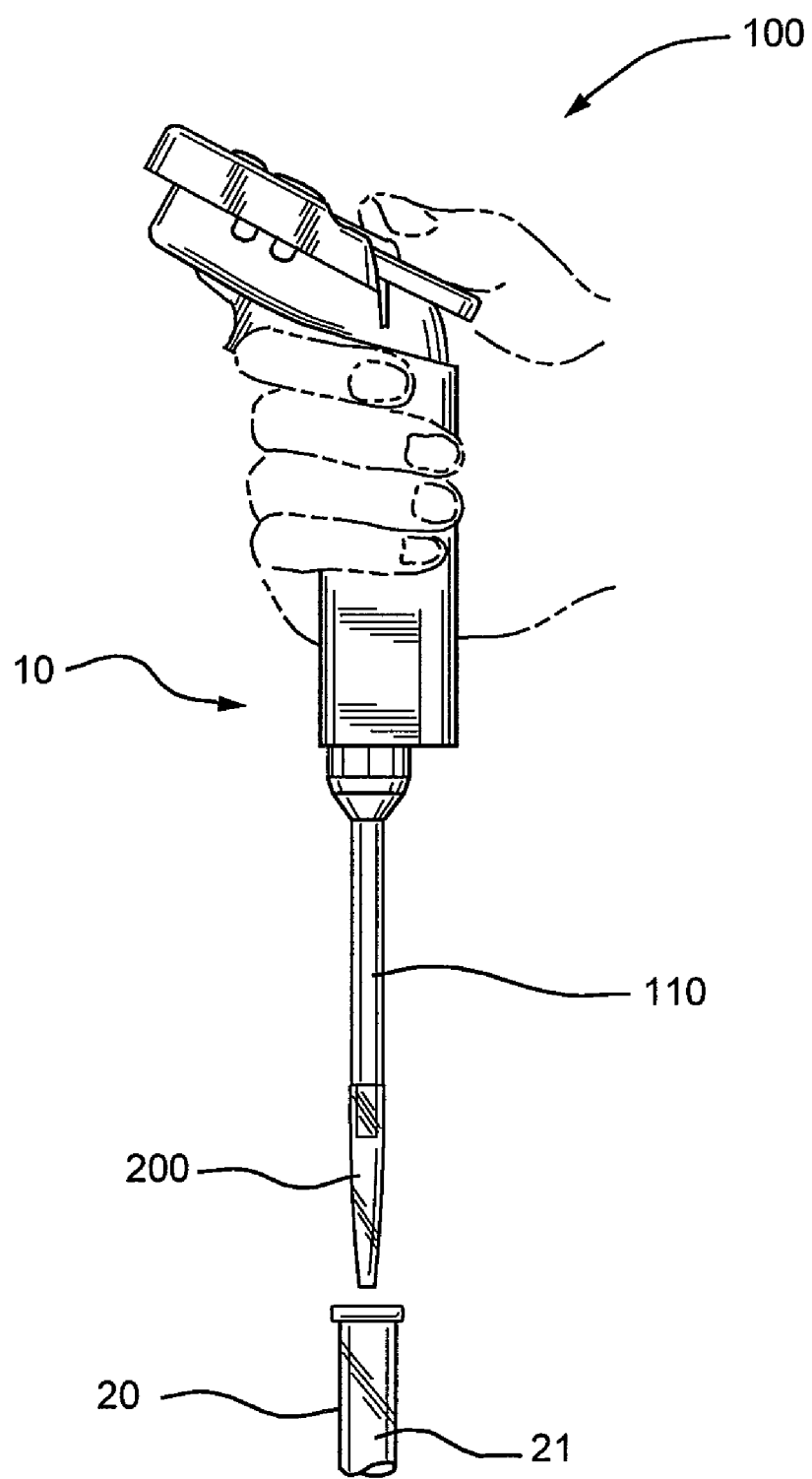
FIG. 2 is a simplified representation of a dispensing device to be calibrated using the sample solutions of the present invention.

A liquid dispenser 100 as shown in FIG. 2 may be used for aspirating and dispensing volumes of liquid into the liquid holder 20. The liquid dispenser includes a channel member 110 and a liquid holding tip 200, or simply, a tip 200. The liquid dispenser 100 may be any of the liquid handling devices used by those ordinarily skilled in the art. It should therefore be understood that the liquid dispenser 100 may include one channel member 110 or may have a plurality of channel members 110, and that regardless of the number of channel members 110 that are included, each channel member 110 may have its own tip 200. Further, the liquid dispenser 100 may be operated manually or automatically in dispensing and aspirating the liquid 21 into and out of the liquid holder 20.

While a form of photometric instrument suitable for use as part of the system is shown in FIG. 1 as a desktop spectrophotometer 30 device, it may alternatively be a small, hand held device that measures absorbance through vessels such as liquid holder 20 containing liquid 21. Such a device may also be a vertical beam spectrophotometer that measures absorbance through vessels such as the wells of microtiter plates. However, it is to be understood that the system and related method are not limited to such a specific photometric instrument and other types of such instruments may be employed including use of a flow cell with a fixed pathlength, or a fiber optic probe to take an absorbance measurement without deviating from the basic function of the system.

A specific vessel represented as liquid holder 20 for containing a solution having a pathlength (inside diameter) of 1.8 centimeters (cm) is used for illustration purposes throughout this description. However, that is only an example and it is to be understood that the present invention is not limited to a specific vessel size or pathlength. The photometric system of the present invention includes an optical sub-system, preferably with four filters to select four wavelengths at which absorbance can be measured. It is to be understood that the system may use more or fewer filters for measurement at different wavelengths or may use another means of wavelength selection. The system includes firmware embodied in the photometric instrument that is programmed to measure absorbance at all necessary wavelengths every time that a volume measurement is made. It is to be understood that the programming may be in software or embedded in hardware. It may be contained locally in the photometric instrument, in another device, or remotely.

The system further includes a kit with one or more vessels of known pathlength (inside diameter) containing a known amount of diluent or a fill mark for the user to add diluent, one or more bottles of sample solution that will be dispensed by a dispenser under test, and a vessel containing a calibration solution. The one or more vessels may or may not be capped and/or capped and sealed.

In the example described herein in which an operator has a kit, the operator of the system removes a vessel containing diluent from the kit of reagents, inserts it into the photometric instrument and presses the "zero" key or other corresponding initiation or activation mechanism. The instrument reads the absorbance at all four wavelengths and sets absorbance at all four wavelengths to zero. In the simplest implementation of this invention, the diluent contains no dye; only a buffer and preservative.

Next, the operator removes the vessel containing diluent from the instrument, dispenses an aliquot of sample solution into the vessel using the delivery device being tested, caps the vessel, mixes the contents by inverting the vessel several times, and returns it into the photometric instrument. Alternatively, the photometric instrument has a built-in mixing means, in which case the operator does not need to remove the vessel from the photometric instrument. In the case where the mixing is accomplished by the device, the vessel may or may not include as part of the design, a structure within the vessel to assist with mixing by generating increased turbulence when spun or otherwise moved during the mixing step. The operator then presses the "read" key or other corresponding initiation or activation mechanism to initiate the photometric measurement following the mixing.

In a specific example using the indicated components, the sample solution contains four dyes, each at a different concentration. More specifically, each dye is selected to be appropriate for a unique range of dispensed volumes. The instrument reads absorbance values for the sample solution starting at the wavelength corresponding to the feature having the lowest absorbance per unit pathlength and if the value is out of range, the instrument would measure the absorbance at the wavelength corresponding to the feature with the next lowest absorbance per unit pathlength. It is to be noted that one or more of the absorbance values may be out of range for the photometric instrument and so measurements should be taken at each of the wavelengths until a useable value is obtained. It should be noted that this example is not intended to limit the ways the measurements are made, as they could start at any wavelength of interest and continue in any pattern until the desired absorbance reading is obtained.

The programming of the software or firmware of the invention is optionally configured to automatically choose the wavelength that has the highest absorbance, yet which is not out of range. Using the Beer-Lambert Law, which states that the absorbance A is the product of dye molar absorptivity $\epsilon$, dye concentration C, and pathlength l:

$$A = \epsilon C l \quad (0.1),$$

the program calculates the volumetric results based on the optical properties of the sample and diluent solutions at the chosen wavelength, a dimension of the vessel, the results of the absorbance measurements and the volume of diluent in the vessel at the start, all as described in one or more of the references incorporated herein. For ease of discussion, the terms $\epsilon$ and C are combined to represent absorbance per unit pathlength at the wavelength of interest. It is to be understood that the relevant dimension of the vessel employed in the equation is dependent upon the type of spectrophotometer used. For a horizontal beam measurement, the vessel dimension relevant to the pathlength of light through the solution is the inside diameter of the vessel. For a vertical beam measurement, the pathlength of light determination is dependent upon the height of the solution in the vessel, also as described in one or more of the incorporated references.

The operator can repeat the dispense operation into the same vessel a number of times. The upper limit on how many times may be set in the program and may depend on: 1) the maximum volume capacity of the vessel, 2) the maximum absorbance limit for the instrument, 3) the minimum absorbance change required for acceptable results, or 4) a limiting number that is preprogrammed.

Once the operator is finished testing a given volume, the results may be sent to the printer 45, display 44 and/or a separately linked computing device. The mean volume, standard deviation, and coefficient of variation are among the types of information that may be sent to the printer 45, display 44 and/or separately linked computing device.

The operator can test delivery devices at several different volumes if desired, dispensing the same sample solution into the vessel as above, subject to the limitations noted above regarding dispensing, and preferably, as long as the smaller volumes are dispensed first and the larger ones subsequently. The reason for this restriction is that to measure a small volume accurately, a spectral feature in the solution must have a sufficiently high absorbance per unit pathlength to get a large enough change in absorbance to measure accurately. If, however, the operator already added so much sample solution that the absorbance is out of range for the photometer, then the system cannot get an accurate measure of that small volume. As stated previously, the term absorbance per unit pathlength is the product of the molar absorptivity of the dye and the concentration of the dye. In this application, the absorbance per unit pathlength is associated with a spectral feature which may or may not result from a combination of dyes.

In the Artel PCS® system, each concentration of sample solution covers a roughly four- or five-fold range of liquid delivery volumes. Therefore, a single sample solution with a single absorbance spectral feature is sufficient for equipment calibration over a four- or five-fold range of volumes. However, if calibration over a greater volume range is desired, more than one solution is required to cover the greater range. For example, if a greater range of volumes were tested with a given relatively dilute concentration of solution suitable for relatively large volumes, the smaller volumes would produce too small a change of absorbance to be measured accurately, leading to an unacceptably large uncertainty in the results. Or, alternatively, if the solution were made more concentrated to boost the signal for the smaller volumes, then the relatively large volumes would produce too high an overall absorbance, leading to non-linear or non-reproducible results. The exception to this volume range limit is for the most dilute solutions, which are used to measure the largest volumes. In this case, the volume of solution being measured is so large that instead of the limit being set by absorbance, it is set by the capacity of the vessel that receives the solution.

In order to address the absorbance or volume range limitation, the simplification provided by the present system and related method involves providing a dye or a plurality of dyes producing multiple distinct detectable light absorbance spectral features in a sample solution such that the combination of detectable light absorbance spectral features in the solution allow calibration or testing over a larger volume range or dilution range of interest than would otherwise be allowed using a single spectral feature. When a relatively large volume is dispensed, the system uses a spectral feature with a low absorbance per unit pathlength as the basis for calculating the volume dispensed. When a small volume is dispensed, the system uses a spectral feature with a high absorbance per unit pathlength as the basis for calculating the volume dispensed. If each spectral feature can cover a volume or dilution range of about 4:1 or about 5:1, and four non-overlapping and distinct spectral features exist within the absorbance spectrum, then a volume range of 2 µl to 5000 µl or a dilution range of 1:1 to 1:2500 can be evaluated for a delivery device using only one sample solution containing all four such spectral features. By incorporating multiple spectral features into one sample solution, the testable volume range is significantly expanded as compared to the sample solutions used by either of the PCS® or the MVS® systems.

For the purpose of making an absorbance measurement, it is always desirable to measure at a wavelength where the spectrum has zero slope, so that a slight error in wavelength will result in little or no corresponding error in absorbance value. Zero slope occurs either at a minimum or a maximum or a plateau in the absorbance spectrum. A single sample solution created through the present system with a dye or a plurality of dyes should provide a complete absorbance spectrum with at least four distinct detectable light absorbance spectral features (i.e., any combination of peaks and/or valleys and/or plateaus) where the slope at each spectral feature is zero. The absorbance values for the peaks or valleys or plateaus must fall within a defined absorbance range which is suitable for measuring a designated range of volumes. If a combination of four different dyes is chosen, then there is complete control over the magnitude of absorbance at all four peaks and/or valleys and/or plateaus. On the other hand, it may be possible to use a single dye having two or more distinct detectable light absorbance spectral features that happen to have suitable magnitudes, but the relationship between the magnitudes of each feature is beyond the control of the user.

By way of example and not intending to be limiting, Table 1 summarizes design parameters based on a system using four absorbance peaks, a path length of 1.8 cm; a maximum absorbance of 1.5 Optical Density (OD); and a diluent volume of 5000 µl. One skilled in the art would recognize that the term Optical Density (OD) could also be referred to as Absorbance Units (AU) or Extinction (E).

TABLE 1

| Volume range of liquid dispenser being tested | Absorbance of sample solution per cm at the wavelength of interest | Measured Absorbance for the smallest volume in the range (must exceed 0.05 OD) |
|---|---|---|
| 2-10 µl | 84.2 at 520 nm | 0.061 |
| 10-50 µl | 17.5 at 430 nm | 0.063 |
| 50-200 µl | 5.00 at 730 nm | 0.086 |
| 200-5000 µl | 1.67 at 630 nm | 0.101 |

Most simple and reasonably priced photometric instruments are able to measure in the visible and near infrared region of the spectrum. Glass absorbs light at ultraviolet wavelengths and silicon photodiodes are not as sensitive at that part of the spectrum. A special source is required for UV wavelengths, typically a deuterium lamp, which would add to the cost of the system. The most basic system will stay within the wavelength range of 340 to 800 nanometers (nm). The dyes chosen for the examples given in this disclosure have principal peaks within this range; however there is no reason that dyes with peaks or valleys or plateaus outside of this range could not be used, provided they were used in conjunction with an instrument that could measure in the expanded range.

Figure 3:
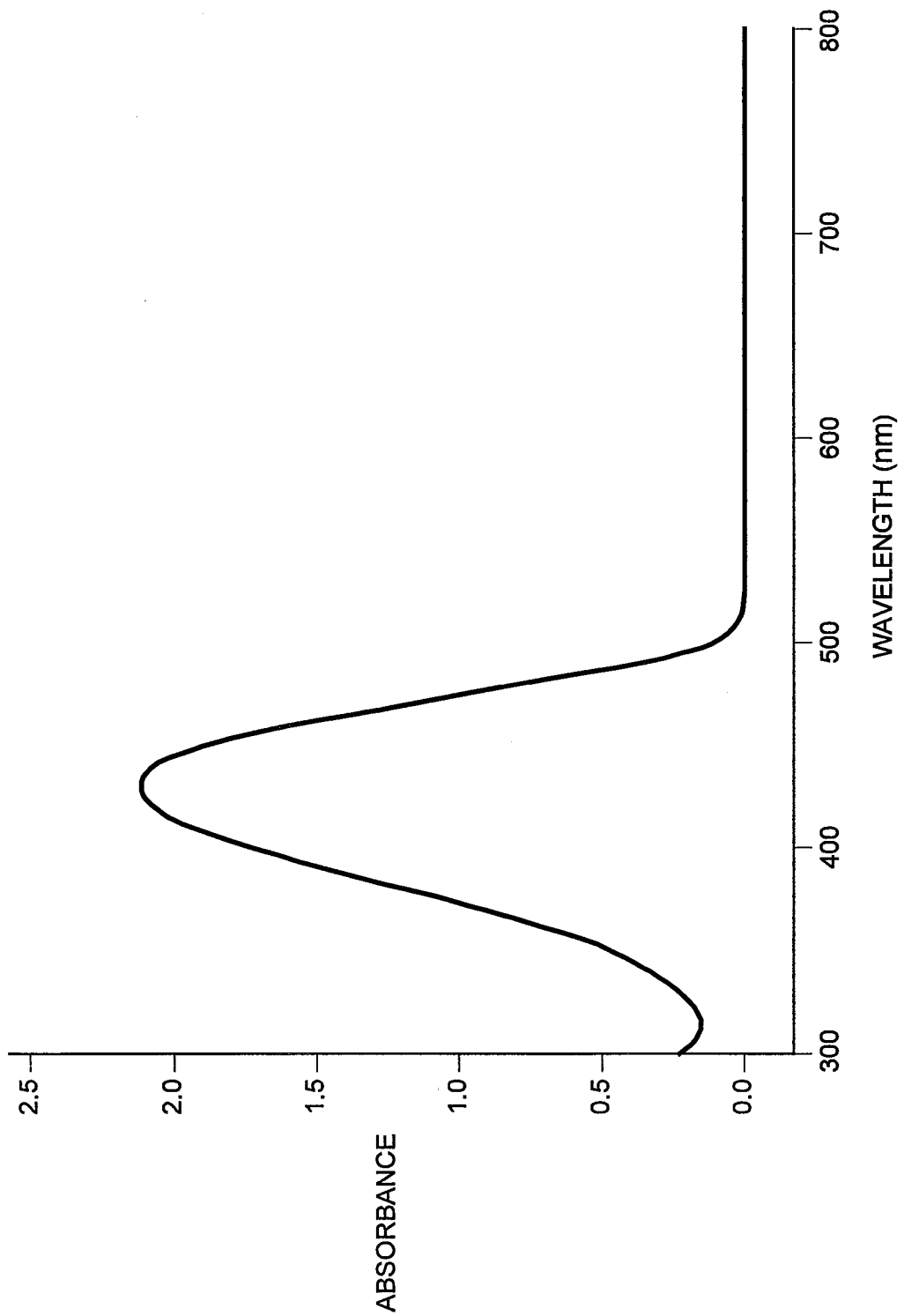
FIG. 3 is a graph of the absorbance spectrum for the dye Tartrazine.

Many organic dyes have an absorbance spectrum with a principal peak at one wavelength, and lesser peaks and valleys at shorter wavelengths which need to be considered when combining dyes. Often, the absorbance decreases sharply to zero at wavelengths longer than the principal peak. An example of such a spectrum is that for Tartrazine, represented by the absorbance curve shown in FIG. 3, in which the principal peak is at about 425 nm. This property is useful when combining multiple dyes in one sample solution since, when the most concentrated dye is chosen to be the one at the short end of the wavelength range, it does not interfere with the spectra of the dyes that are added with principal absorbance peaks at longer wavelengths. In this way, multiple dyes can be combined in a way that their spectra have relatively little interference with one another.

Two examples of sample solutions with multiple distinct detectable light absorbance spectral features are described herein; one uses four dyes and the other uses two. These are only examples and are not intended to represent all options for using one or more dyes in a single sample solution to establish multiple distinct detectable light absorbance spectral features.

The four dyes of the first example are chosen based on the following criteria:

Peaks are approximately equally spaced and are within the visible range when the dyes are combined;

Peaks are broad enough so that they are easily measured with an instrument of modest wavelength accuracy (e.g. ±5 nm);

They are all adequately soluble in aqueous solution;

Their physical properties in aqueous solution do not adversely affect the ability of a liquid delivery device to accurately dispense the resulting solution (e.g. if surface tension of the solution is reduced, there will be a tendency for small droplets to remain behind in the tip of the delivery device);

They are not unstable in solution (e.g. due to light exposure) or pH dependent (e.g. indicators); and The tail on the long wavelength side of the principal peak of one dye does not overlap with the peak of the next dye. This helps to assure that the next peak really is a peak, and not just a bump on the tail of the peak below it.

Figure 4:
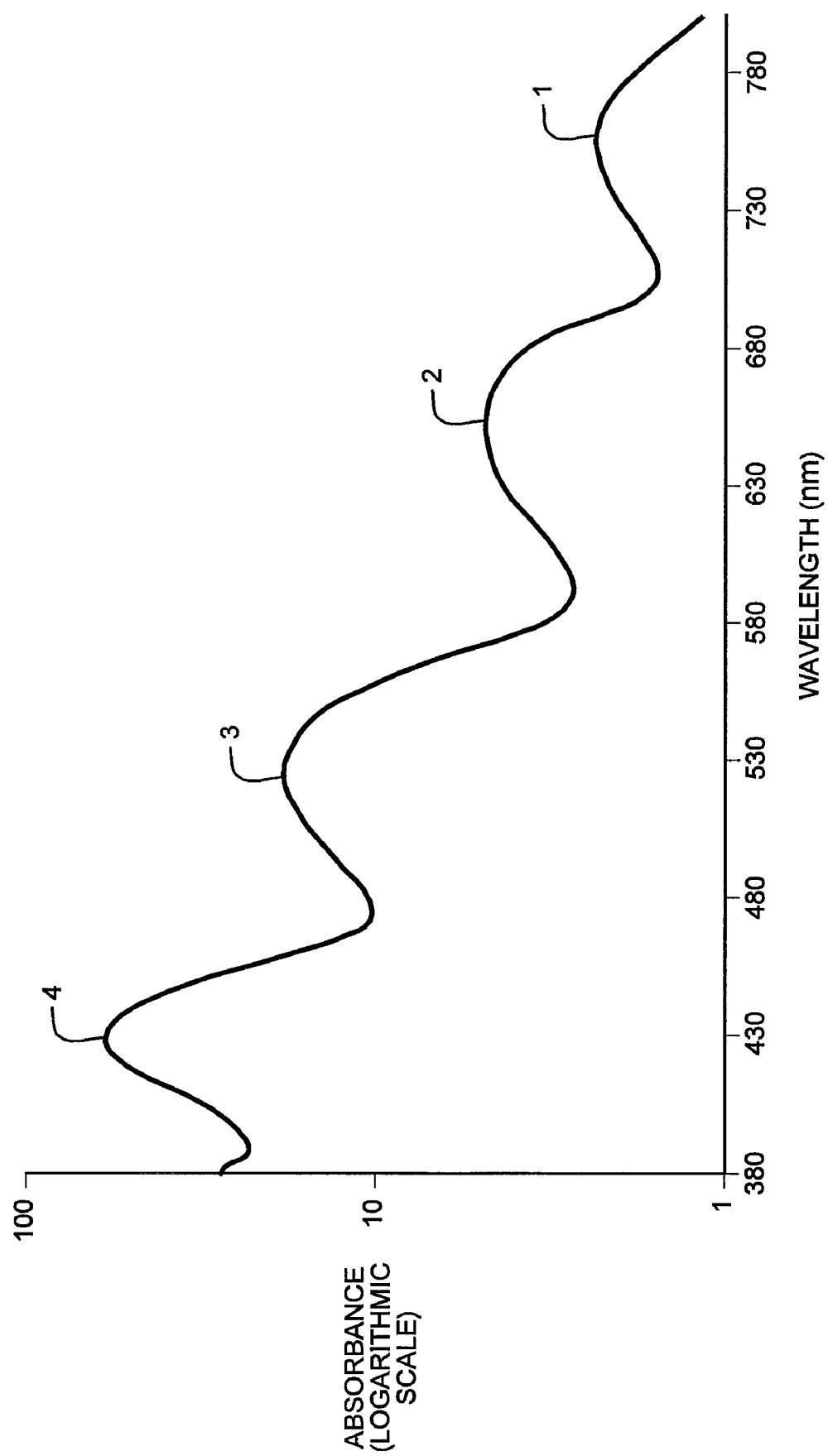
FIG. 4 is a graph of the ideal absorbance spectrum over a complete absorbance range of an example single solution containing four dyes of different concentrations.

In the conceptually simplest example of a single solution containing four dyes, there are four peaks and each peak does not interfere with its neighboring peaks. The absorbance spectral features for this four-dye example are represented in FIG. 4. In that figure, Feature 1, which is the peak for $Cu(EDTA)^{2-}$ and has the lowest absorbance per unit pathlength of the four dyes, could be used for the largest volumes (200-5000 µl) to be tested. Feature 2, which is the peak for Methyl Green, could be used for the next volume range down (50-200 µl). Feature 3, which is the peak for Ponceau S, could be used for the next volume range down (10-50 µl). Finally, Feature 4, which is the peak for Tartrazine and has the highest absorbance per unit pathlength of the four dyes, could be used for the smallest volumes (2-10 µl) to be tested.

The four dyes used in this example and meeting the criteria identified above are given in Table 2:

TABLE 2

| Dye | Wavelength at Peak Absorbance | Desired absorbance per cm |
|---|---|---|
| $Cu(EDTA)^{2-}$ | 730 nm | 1.67 |
| Methyl Green | 629 nm | 5.00 |
| Ponceau S | 520 nm | 17.5 |
| Tartrazine | 425 nm | 84.2 |

Dilution ratios for the concentrations of this sample solution which target each dye are 0.5 for the $Cu(EDTA)^{2-}$, 0.17 for the Methyl Green, 0.05 for the Ponceau S, and 0.01 for the Tartrazine. It is to be understood that other dyes may be used, other or the same dyes may be used in different concentrations, to achieve the intended outcome of the present invention and that the example represented in the table is in no way intended to be limiting.

Figure 5:
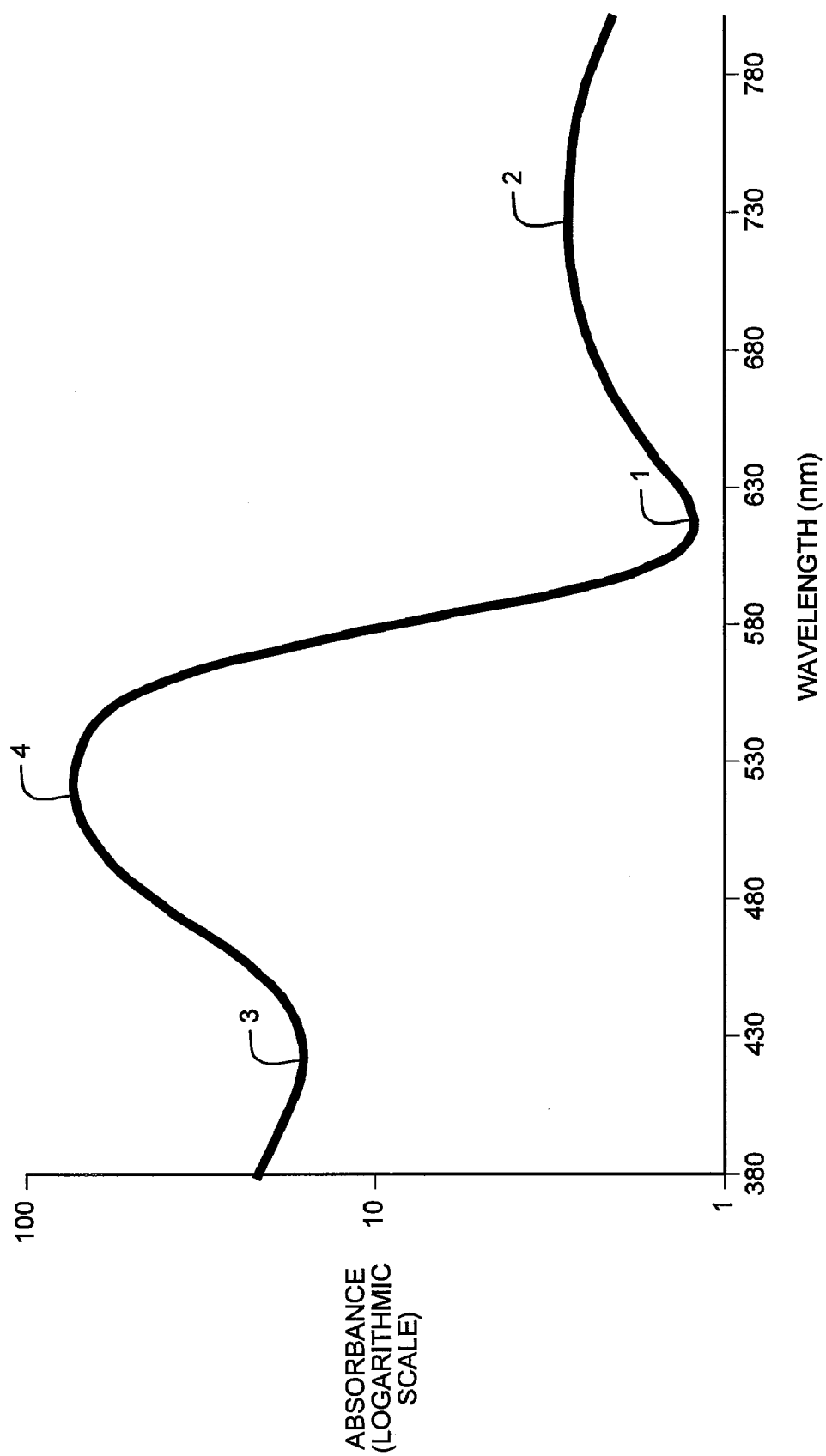
FIG. 5 is a graph of the actual absorbance spectrum of an example single solution containing two dyes over a complete absorbance range.
Figure 6:
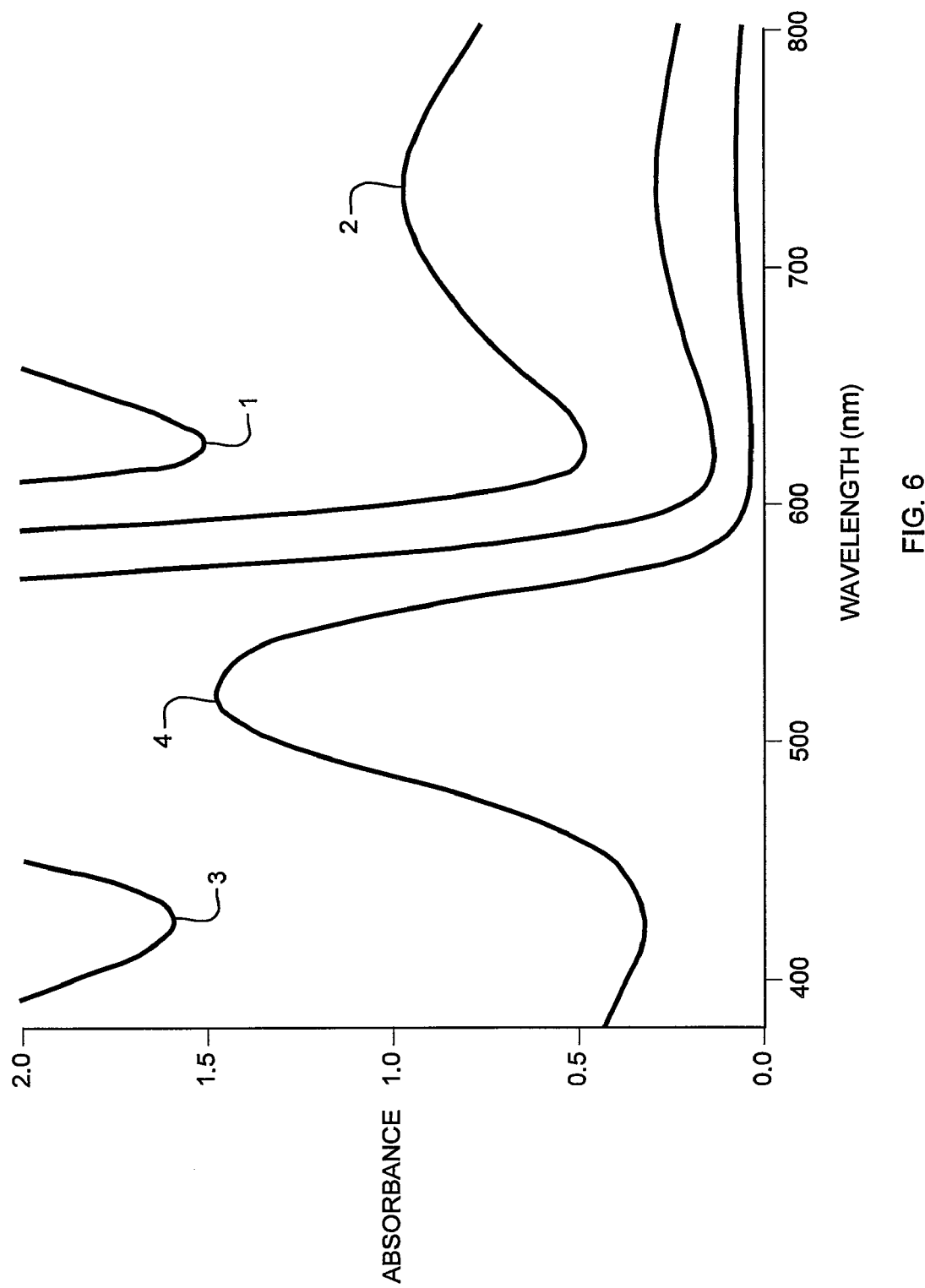
FIG. 6 is a graph of the actual absorbance spectrum of the example single solution of FIG. 5 at four different concentrations over a specific limited absorbance range.

In the event the four-dye relationship shown in FIG. 4 is difficult to achieve, such as due to limitations of the spectrophotometer or the dyes available, a smaller number of dyes may be used, provided their characteristics provide the desired number of distinct detectable light absorbance spectral features to cover the volume ranges of interest. An example alternative for that purpose is the two-dye combination represented in FIGS. 5 and 6. FIG. 5 represents the absorbance curve for the two-dye sample solution for a complete absorbance range using a logarithmic scale and FIG. 6 represents four different dilutions of the two-dye sample solution, each dilution being chosen to bring one of the spectral features within the absorbance range typically available with commercial photometric instruments. In this alternative example, the two dyes produce two peaks and two valleys to give distinct spectral features from which to calculate the volume dispensed. Feature 1, a valley between the peak of the $Cu(EDTA)^{2-}$ and the principal Ponceau S peak, could be used for the largest volumes (200-5000 µl). Feature 2, the $Cu(EDTA)^{2-}$ peak, could be used for the next volume range down (50-200 μl). Feature 3, a valley from the Ponceau S minimum between the principal and secondary peaks, could be used for the next range (10-50 μl). Finally, Feature 4, the principal Ponceau S peak could be used for the smallest volumes (2-10 μl).

The two dyes used for this example have the characteristics given Table 3:

TABLE 3

| Dye/Spectral Feature | Wavelength of Feature | Desired absorbance per cm |
|---|---|---|
| Cu(EDTA)$^{2-}$ | 730 nm | 5.00 |
| Valley between Cu(EDTA)$^{2-}$ and Ponceau S | 629 nm | 2.68 |
| Ponceau S | 520 nm | 84.2 |
| Ponceau S Valley | 425 nm | 18.2 |

In this example, the desired absorbance per cm for the valley between the Cu(EDTA)$^{2-}$ and Ponceau S is fixed based on the ratio of the two dyes in the solution. Also, the absorbance per cm for the Ponceau S valley is related to the absorbance per cm of the peak as it is a property of that dye.

The results of a volume measurement using a multi-dye solution of the present invention are calculated using the Beer Lambert Law identified in equation (0.1) herein. Specifically, for the first delivery of sample solution with volume $V_1$ the expected absorbance at wavelength i is $$A_1^i = \varepsilon_i C_i l \left( \frac{V_1}{V_1 + V_D} \right) \quad (0.2)$$

Where $A_1^i$ is the absorbance after the first delivery measured at wavelength i, $\varepsilon_i C_i$ is the absorbance per unit pathlength of the sample solution at wavelength i; and $V_D$ is the volume of diluent originally in the vessel.

This can be solved for the delivery volume $V_1$:

$$V_1 = V_D \left( \frac{A_1^i}{\varepsilon_i C_i l - A_1^i} \right) \quad (0.3)$$

This equation holds for all of the absorbance measurements at all wavelengths. However, some of the absorbance measurements are unsuitable for use; either they are so small that there is too much uncertainty associated with them, or they are too large for the instrument to measure accurately. If the concentrations of the different dyes have been chosen correctly, then at least one of the absorbance measurements is in a measurable absorbance range and can be used to calculate an accurate value of volume.

After the $n^{th}$ delivery of sample solution, the total volume of sample solution delivered up to and including the $n^{th}$ can be calculated in the same way:

$$V_T(n) \equiv \sum_{j=1}^{n} V_j = V_D \left( \frac{A_n^i}{\varepsilon_i C_i l - A_n^i} \right) \quad (0.4)$$

The system of the present invention includes the option, manually or automatically through programming, such as associated with the firmware, for example, but not limited thereto, to keep a running tally of how much sample has been added through the $n-1^{th}$ delivery, so it can simply be subtracted to find the value added at the $n^{th}$ delivery:

$$V_n \equiv V_T(n) - V_T(n-1) = V_D \left( \frac{A_n^i}{\varepsilon_i C_i l - A_n^i} - \frac{A_{n-1}^j}{\varepsilon_j C_j l - A_{n-1}^j} \right) \quad (0.5)$$

Note that the value of $V_n$ is only dependent on the $n^{th}$ and $n-1^{th}$ absorbance measurements, and that these two sequential measurements need not have been made at the same wavelength. In equation (0.5) the $n^{th}$ measurement was made at wavelength i, and the $n-1^{th}$ was made at wavelength j.

An example of how volumetric results could be calculated for the example case of four dyes noted above follows. In this example, the user dispenses one aliquot of 5 μl, one of 20 μl, one of 100 μl and one of 1000 μl. The initial volume of diluent is 5000 μl. The vessel pathlength is 1.8 cm. The expected absorbance values at the four wavelengths and the calculated volumes are provided in Table 4:

TABLE 4

| | | Volume of Diluent | | 5000 ul | | | |
| | | Pathlength | | 1.8 cm | | | |
| | | Max absorbance | | 1.5 | | | |

| Volume Added | Total Sample Volume | Total Volume in Vial | Wavelength | Abs per cm of Sample Sol'n | Absorbance | Calculated Total Sample | Calculated Sample Added |
|---|---|---|---|---|---|---|---|
| 5 | 5 | 5005 | 730 | 1.67 | 0.003003 | | |
| | 5 | 5005 | 629 | 5 | 0.008991 | | |
| | 5 | 5005 | 520 | 17.5 | 0.031469 | | |
| | 5 | 5005 | 425 | 84.2 | 0.151409 | 5 | 5 |
| 20 | 25 | 5025 | 730 | 1.67 | 0.014955 | | |
| | 25 | 5025 | 629 | 5 | 0.044776 | | |
| | 25 | 5025 | 520 | 17.5 | 0.156716 | | |
| | 25 | 5025 | 425 | 84.2 | 0.75403 | 25 | 20 |
| 100 | 125 | 5125 | 730 | 1.67 | 0.073317 | | |
| | 125 | 5125 | 629 | 5 | 0.219512 | | |
| | 125 | 5125 | 520 | 17.5 | 0.768293 | 125 | 100 |
| | 125 | 5125 | 425 | 84.2 | 3.696585 | | |
| 1000 | 1125 | 6125 | 730 | 1.67 | 0.552122 | 1125 | 1000 |
| | 1125 | 6125 | 629 | 5 | 1.653061 | | |
| | 1125 | 6125 | 520 | 17.5 | 5.785714 | | |
| | 1125 | 6125 | 425 | 84.2 | 27.83755 | | |

Table 4 gives the absorbance values at each of the four wavelengths after each delivery. For each volume determination, the absorbance selected for use in the calculation is the one that is as large as possible yet also within the measurable absorbance range (less than 1.5 in this example). Those values are shown in the table. In making the calculation, the absorbance per cm for the spectral feature at the measured wavelength is used in the equations above.

The scenarios presented above have described using multiple light absorbance spectral features present in the sample solution to determine the accuracy of volume delivery from a test device. The examples presented demonstrate that by using multiple light absorbance spectral features in the sample solution, a significantly enlarged testable volume range can be achieved, as compared to individual solutions with only one light absorbance spectral feature. Yet another way to further expand the testable volume range would be to include one or a plurality of dyes in the diluent solution, which present one or a plurality of distinct light absorbance spectral features, these features being unique to the diluent solution. Because these light absorbance spectral features are unique to the diluent solution, they are not in common with, nor overlap significantly with any light absorbance spectral feature or features in the sample solution. The light absorbance spectral features in the diluent can also be used to quantify volume additions.

As an example of this alternative approach, the absorbance values of the light absorbance spectral features in the diluent are measured prior to any sample volume addition. As in the examples above, some of these features will be too highly absorbing, but others will be within range. The desired test volume of sample solution is then added to the diluent and mixed, and the absorbance values of the light absorbance spectral features in the mixture of sample and diluent are measured. The addition of sample solution dilutes the concentration of dyes in the diluent, reducing the absorbance values for the light absorbance spectral features of the diluent dyes. The decrease in absorbance for the diluent spectral features in the mixture is directly related to the volume of sample solution that was added. Thus, by applying the same concepts as explained for the sample solution above, multiple light absorbance spectral features in the diluent can be used to measure sample volume.

A clear extension of the above example would be to use a sample solution with multiple light absorbance spectral features as well as a diluent with multiple light absorbance spectral features that are unique to the diluent and different from the sample. By monitoring the absorbance of the multiple light absorbance spectral features in the sample and in the diluent, an even further extension of testable volume range can be achieved. Because the light absorbance spectral features in the diluent are measured by their dilution, measurable changes to these features occur typically due to larger sample volume additions. Thus, the features in the diluent should be most applicable to large sample volume additions, whereas the small sample volume additions will be more appropriately measured by the light absorbance spectral features in the sample solution.

It can be seen from this alternative example that the present invention may be used to calculate the volume of a sample solution added to a vessel wherein the sample solution may include one or a plurality of dyes presenting one or a plurality of distinct light absorbance spectral features, the diluent may also include one or more dyes presenting one or a plurality of distinct light absorbance spectral features, further distinct from the features of the sample solution, all in any combination to cover a wider range of volumes than has heretofore been available.

It is desirable that means be provided to allow the user to periodically test the instrument for correct and accurate functionality. One method of doing that is to provide a vessel containing calibration solution in the reagent kit. This calibration solution preferably contains all of the same dyes present in the sample solution(s); however, the concentrations will be such that the absorbance values are within a measurable range at all of the wavelengths without dilution, at least with respect to the four-dye example. The user inserts the vessel into the instrument, and instructs it to check the calibration. Readings are made at all of the wavelengths and compared to the values measured in the kit manufacturer's laboratory using an instrument whose results are traceable to international standards. Pass/Fail criteria are provided by the manufacturer of the system. The calibration vessel will not be consumed or altered in this process, so the calibration can be carried out as often as desired. For the situation in which fewer than four dyes are used, more than one calibration standard might be required in order to provide a calibration point within the measurable absorbance range for each utilized wavelength.

As previously indicated, the concept of using one or more sample solutions, with each sample solution including multiple light absorbance spectral features, may also be applied to evaluations of dilution protocols. U.S. patent application Ser. No. 11/854,594 incorporated herein provides details of three dilution-related methods involving the use of different calculation mechanisms for determining either volume or dilution ratios based on dilution protocols performed. The reference describes dilution evaluations based on the use of a single light absorbance spectral feature in solutions used to carry out the determinations. The present invention includes methods in which solutions having multiple light absorbance spectral features are used in the dilution evaluations in which a sample solution is combined with a diluent one or more times.

A first dilution-related method provides the capability to measure the volume of a sample solution in a vessel over a volume range that is wider than can be measured when a single light absorbance spectral feature component is employed while also eliminating uncertainty due to vessel dimension variability. Specifically, the first dilution-related method for use with a vessel having a bottom and known dimensions, includes the steps of: a) adding to the vessel a diluent including a known concentration of a diluent dye, resulting in a diluent with a light absorbance spectral feature at a wavelength unique to the diluent and having no measurable absorbance at the wavelengths of interest for the sample solution; b) measuring the absorbance at the wavelength unique to the diluent; c) adding a volume of the sample solution to the vessel, wherein the sample solution has no measurable absorbance at the wavelength unique to the diluent, and includes one or more dyes, at known concentration(s), to establish multiple light absorbance spectral features at a corresponding plurality of wavelengths; d) mixing the diluent and the sample solution in the vessel to produce a mixture of the sample solution and the diluent; e) measuring the absorbance of the mixture of the sample solution and the diluent at all wavelengths; and f) calculating the volume of the sample solution added to the vessel based on the measured absorbance values.

Calculating the volume in the first dilution-related method requires that the volume of diluent added to the vessel be known. If it is not known, it is calculated from the absorbance per unit pathlength of the diluent at the wavelength unique to the diluent, the pathlength of light through the diluent as determined using the measured absorbance of the diluent dye at the wavelength, prior to adding the sample solution to the vessel, and the dimensions of the vessel. The first dilution-related method includes using the following equation to calculate the volume:

$$V_s = V_d \cdot \frac{a_d}{a_s} \cdot \frac{A_{\lambda 1}}{A_{\lambda 2}} \qquad (0.6)$$

where ($V_s$) is the volume of the sample solution added to the vessel, ($V_d$) is the volume of the diluent added to the vessel, ($a_d$) is the absorbance per unit pathlength of the spectral feature in the diluent, ($a_s$) is the absorbance per unit pathlength of a spectral feature of the sample solution having a measurable absorbance for a volume range, ($A_{\lambda 1}$) is the absorbance of the spectral feature of the sample solution at a wavelength that is measurable, and ($A_{\lambda 2}$) is the absorbance of the spectral feature in the diluent at the wavelength distinct from the measurable wavelength of the spectral feature of the sample solution. That is, the single sample solution may be used over a broad volume range by providing at least one distinct light absorbance spectral feature per volume range subset without requiring replacement of a first sample solution with one known dye concentration with a second sample solution with a second known concentration of the same dye, which second concentration is greater or less than the known concentration of the first sample solution. In the example previously described regarding a sample solution with four dyes, the sample solution may be employed in the first dilution-related method for volume measurements over a volume range that would previously have only been achievable with four separate sample solutions, each having a single distinct light absorbance spectral feature. Similarly, the two-dye sample solution from above could cover the same volume range because each dye results in two distinct detectable light absorbance features, for a total of four distinct spectral features in the solution, with each distinct feature covering a different volume range.

An additional approach that can be added to this first dilution-related method is to incorporate multiple dyes into the diluent which impart multiple light absorbance spectral features to the diluent which are unique to the diluent and different from the light absorbance spectral features present in the sample solution. The added light absorbance spectral features of the diluent provide the capability to measure the volume of a sample solution in a vessel over a volume range that is wider than can be measured when only light absorbance spectral features in the sample are used. This approach involves the steps of: a) adding to the vessel a diluent including a known concentration or concentrations of one or a plurality of diluent dyes, resulting in a diluent with a plurality of light absorbance spectral features at wavelengths unique to the diluent and having no measurable absorbance at the wavelengths of interest for the sample solution; b) measuring the absorbance at the wavelengths unique to the diluent; c) adding a volume of the sample solution to the vessel, wherein the sample solution has no measurable absorbance at the wavelengths unique to the diluent, and includes one or more dyes, at known concentration(s), to establish multiple light absorbance spectral features at a corresponding plurality of wavelengths; d) mixing the diluent and the sample solution in the vessel to produce a mixture of the sample solution and the diluent; e) measuring the absorbance of the mixture of the sample solution and the diluent at all wavelengths; and f) calculating the volume of the sample solution added to the vessel based on the measured absorbance values.

A second dilution-related method of the present invention provides the capability to determine the dilution of a sample solution over a volume range or a dilution range that is wider than is available in a similar volume or dilution determination when only a single light absorbance spectral feature can be measured. The sample solution includes a plurality of dyes and the diluent includes a dye that is the same as one of the plurality of dyes of the sample solution and is included in substantially the same concentration as in the sample solution for that common dye. Specifically, the second dilution-related method includes the steps of: a) measuring in the sample solution the absorbance values of each of the plurality of spectral features at respective independent wavelengths for which measurable absorbance values may be obtained, wherein the sample solution is contained in a first vessel of a plurality of vessels; b) transferring a target volume of the sample solution from the first vessel to a second vessel of the plurality of vessels; c) mixing into the sample solution in the second vessel a target volume of the diluent; d) measuring the absorbance values of the spectral features in the second vessel for which measurable absorbance values may be obtained, but for which a measurable absorbance must be obtained for the common dye; and e) calculating a dilution ratio for the sample solution contained in the second vessel, wherein the dilution ratio represents the extent to which the sample solution has been diluted by the diluent mixed into the second vessel.

The calculation of the dilution ratio associated with the transfer of the sample solution from the first vessel into the second vessel, and then diluting that mixture involves using the equation $$R_{12} = \frac{A_{1,\lambda 1}}{A_{2,\lambda 1}} \cdot \frac{A_{2,\lambda 2}}{A_{1,\lambda 2}} \qquad (0.7)$$

where ($A_{1,\lambda 1}$) is the absorbance of any of the plurality of spectral features, only of the sample solution, that provide an absorbance within a defined measurable absorbance range and that are measured in the first vessel, ($A_{2,\lambda 1}$) is the absorbance of any of the plurality of spectral features, only of the sample solution, that provide an absorbance within a defined measurable absorbance range and that are measured in the second vessel, ($A_{1,\lambda 2}$) is the absorbance of the spectral feature that is common to both the sample solution and the diluent measured in the first vessel containing only the sample solution, ($A_{2,\lambda 2}$) is the absorbance of the spectral feature that is common to both the sample solution and the diluent measured in the second vessel, and ($R_{12}$) is the dilution ratio.

The second dilution-related method may be extended across further dilution steps beyond a transfer from the first vessel to the second vessel by: a) repeating X more times the steps of i) transferring a target volume of the mixture of the sample solution and the diluent into a subsequent vessel, ii) mixing in a target volume of the diluent into the subsequent vessel, and iii) measuring the absorbance values for all spectral features for which measurable absorbance values may be obtained, wherein X is $\geq 1$, such that the last vessel of the plurality of vessels with the mixture of the sample solution and the diluent and the added diluent is vessel n and a preceding vessel is vessel m; and b) calculating a dilution ratio for the mixture of the sample solution and the diluent contained in vessel n, wherein the dilution ratio represents the extent to which the mixture of the sample solution and the diluent has been diluted by the diluent mixed into vessel n. A running tally may be kept of how much diluted sample has been added from a preceding vessel into a specific vessel through the $n^{th}$ delivery based on the dilution ratio. The dilution ratio may be calculated for any number of dilution steps of a dilution protocol across a relatively larger volume range with the second dilution-related method of the present invention using the equation $$R_{mn} = \frac{A_{m,\lambda1}}{A_{n,\lambda1}} \cdot \frac{A_{n,\lambda2}}{A_{m,\lambda2}} \quad (0.8)$$

where ($R_{mn}$) is the dilution ratio for the mixture of the sample solution and the diluent in vessel m after mixing with the diluent in vessel n, ($A_{m,\lambda1}$) is the measurable absorbance of any of the plurality of spectral features only of the sample solution measured in vessel m, ($A_{n,\lambda1}$) is the measurable absorbance of any of the plurality of spectral features only of the sample solution measured in vessel n, ($A_{m,\lambda2}$) is the absorbance of the spectral feature that is common to both the sample solution and the diluent measured in vessel m, and ($A_{n,\lambda2}$) is the absorbance of the spectral feature that is common to both the sample solution and the diluent measured in vessel n.

It can be seen that a single sample solution may be diluted over a broad volume range by providing at least one distinct light absorbance spectral feature per volume range subset without requiring replacement of a first sample solution with one known dye concentration with a second sample solution with a second known concentration of the same dye, which second concentration is greater or less than the known concentration of the first sample solution. In the example previously described regarding a sample solution with four dyes, the sample solution may be employed in the second dilution-related method, provided it also included a fifth dye with a distinct measurable light absorbance spectral feature in common with the dye of the diluent, to assess dilution over a volume range that would previously have only been achievable with four separate sample solutions, each having a single distinct light absorbance spectral feature (again, each being distinct from the light absorbance spectral feature of the dye in common with the dye of the diluent). Similarly, the two-dye sample solution example from above could cover the same volume range if a third dye were added, which third dye would be present in both the sample solution and the diluent in substantially equal concentrations. In using either a four-dye or a two-dye version of the invention, this second dilution-related method may be used to reduce uncertainty due to variable dilution volume, or variable vessel pathlength, for example, when used for testing in microtiter plates measured using vertical beam spectrophotometers.

In an example of the second dilution-related method, a single sample solution and a single diluent could be mixed together and used to calculate the dilution of the sample solution by the diluent over a complete volume range.

A third dilution-related method of the present invention provides a capability similar to that of the second dilution-related method in order to determine the dilution of a sample solution over a volume range and a dilution range that is wider than is available in a similar corresponding dilution determination when only a single light absorbance spectral feature can be measured. The sample solution includes a plurality of dyes and the diluent includes a dye that is the same as one of the plurality of dyes of the sample solution and is included in substantially the same concentration as in the sample solution for that common dye. Specifically, the third dilution-related method includes the steps of: a) transferring a target volume of the sample solution from a source into a vessel; b) mixing into the sample solution in the vessel a target volume of the diluent; c) measuring the absorbance values of the spectral features of the solution in the vessel; and d) calculating a dilution ratio of the sample solution from the source, wherein the dilution ratio represents the extent to which the sample solution of the source has been diluted by the diluent mixed into the vessel.

The third dilution-related method may be extended across further dilution steps beyond a transfer from the source to a single vessel by: a) repeating X more times the steps of i) transferring a target volume of the mixture of the sample solution and the diluent to a subsequent vessel, ii) adding a target volume of the diluent with the known concentration of the common dye to the mixture of the sample solution and the diluent in the subsequent vessel and iii) measuring the absorbance values, wherein X is $\geq 1$, such that any vessel but the source is vessel m and the source is represented as vessel 0; and b) calculating a dilution ratio for the sample solution from the source, wherein the dilution ratio represents the extent to which the sample solution of the source has been diluted by the diluent through all mixing steps. The dilution ratio may be calculated for any number of dilution steps of a dilution protocol across a relatively larger volume range with the third dilution-related method of the present invention using the equation $$R_{0m} = \frac{a_s}{a_d} \cdot \frac{A_{m,\lambda2}}{A_{m,\lambda1}} \quad (0.9)$$

where ($R_{0m}$) is the dilution ratio for the sample solution of vessel 0 after all diluent additions, ($a_d$) is the absorbance per unit pathlength of the common spectral feature, ($a_s$) is the absorbance per unit pathlength of a spectral feature unique to the sample solution, ($A_{m,\lambda1}$) is the measurable absorbance of the spectral feature unique to the sample solution measured in vessel m, and ($A_{m,\lambda2}$) is the measurable absorbance of the common spectral feature measured in vessel m.

It can be seen that a single sample solution may be diluted over a broad volume range by providing at least one distinct light absorbance spectral feature per volume range subset without requiring replacement of a first sample solution with one known dye concentration with a second sample solution with a second known concentration of the same dye, which second concentration is greater or less than the known concentration of the first sample solution. In the example previously described regarding a sample solution with four dyes, the sample solution may be employed in the third dilution-related method, provided it also includes a fifth dye with a distinct measurable light absorbance feature in common with the spectral feature of the diluent, to assess dilution over a volume range that would previously have only been achievable with four separate sample solutions, each having a single distinct light absorbance spectral feature (again, each being distinct from the light absorbance spectral feature of the dye in common with the dye of the diluent).

In an example of the third dilution-related method, a single sample solution and a single diluent could be mixed together and used to calculate the dilution of the sample solution by the diluent over a complete volume range.

A fourth dilution-related method of the present invention provides a capability similar to that of the second and third dilution-related methods in order to determine the dilution of a sample solution over a volume range and a dilution range that is wider than is available in a similar corresponding dilution determination when only a single light absorbance spectral feature can be measured. This fourth dilution related method is similar to the second dilution related method in that it can be used to determine the dilution ratio between any two steps in a multiple dilution step protocol. However, this fourth approach is needed because the dilution steps are too large to allow for an accurate determination of the dilution ratio using equation (0.8). In this fourth dilution-related method, a multi-step dilution protocol is conducted. The sample solution includes a plurality of dyes and the diluent includes a dye that is the same as one of the plurality of dyes of the sample solution and is included in substantially the same concentration as in the sample solution. Specifically, the fourth dilution-related method includes the steps of: a) transferring a target volume of the sample solution from a source into a first vessel; b) mixing into the sample solution in the first vessel a target volume of the diluent; c) transferring a target volume of the mixed sample and diluent from the first vessel into a second vessel, d) mixing into the solution in the second vessel a target volume of the diluent, e) measuring the absorbance values of the spectral features of the solution in the first and second vessels; and f) calculating a dilution ratio for the sample solution contained in the second vessel, wherein the dilution ratio represents the extent to which the mixed sample and diluent from the first vessel has been diluted by the diluent mixed into the second vessel.

This fourth dilution-related method requires a different calculation because neither equation (0.8) nor equation (0.9) is capable of determining the described dilution protocol under all conditions. For example, assume that the delivery of solution from the first vessel to the second vessel involves a dilution step that is larger than can be measured by any one absorbance spectral feature. When using absorbance-based dyes, a measurable linear absorbance can typically only be achieved over a concentration change of 2-3 orders of magnitude. Thus, assume a scenario where the delivery from the source to the first vessel is large. In this case, one light absorbance spectral feature, which will be called s is selected for the analysis. The absorbance per unit pathlength of s is known for the undiluted solution in the source vessel and is given by $a_s$. Since the dilution of the sample solution from the source vessel to the first vessel is sufficiently large, equation (0.8) cannot be used to determine the dilution that has been performed because the absorbance associated with s will be too high to directly measure for the sample solution in the source vessel. However, assuming the dilution step results in a measurable absorbance associated with s in the first vessel, equation (0.9) can be used to determine the dilution that has occurred. Now, assume that the dilution protocol is carried out from the first vessel into the second vessel, and that this dilution step is also large. In this scenario, the absorbance associated with s is measurable in the first vessel, but the dilution protocol may have caused the absorbance associated with s to be too small to be accurately measured in the second vessel.

Because the absorbance associated with s cannot be accurately measured in the second vessel, the dilution cannot be determined using any of the equations presented so far. A new equation needs to be considered for such a scenario, which involves using a second absorbance spectral feature, which will be called s'. The absorbance per unit pathlength of s and s' are known for the sample solution in the source vessel, but are sufficiently large such that the absorbance values of s and s' cannot be directly measured solely for the undiluted sample solution. As described, the dilution that occurs in transferring the sample solution from the source vessel into the first vessel results in a measurable absorbance associated with s. However, in this case, the absorbance associated with s' is still too large to be measurable. Continuing the protocol between the first vessel and the second vessel results in an absorbance associated with s that is too small to be accurately measured, but results in a measurable absorbance associated with s'. For this scenario, the dilution of the sample solution that occurs between the first vessel and the second vessel can be determined by dividing the overall dilution between the source vessel and the second vessel by the overall dilution between the source vessel and the first vessel, as expressed by:

$$R'_{12} = \frac{R_{02}}{R_{01}} \tag{1.0}$$

where ($R_{01}$) is calculated using equation (0.9) with the first vessel as vessel m, the wavelength associated with the common spectral feature in the diluent is $\lambda_2$ and the wavelength associated with the spectral feature s that is unique to the sample solution is $\lambda_1$. Similarly, ($R_{02}$) is calculated using equation (0.9) with the second vessel as vessel m and the wavelength associated with the common spectral feature in the diluent is $\lambda_2$ and the wavelength associated with the spectral feature s' that is unique to the sample solution is $\lambda_1$.

The fourth dilution-related method may be extended across further dilution steps beyond a transfer from the first vessel to the second vessel by: a) repeating X more times the steps of i) transferring a target volume of the mixture of the sample solution and the diluent into a subsequent vessel, ii) mixing in a target volume of the diluent into the subsequent vessel, and iii) measuring the absorbance values for all spectral features for which measurable absorbance values may be obtained, wherein X is $\geq 1$, such that the last vessel of the plurality of vessels with the mixture of the sample solution and the diluent and the added diluent is vessel n and a preceding vessel is vessel m; and b) calculating a dilution ratio for the mixture of the sample solution and the diluent contained in vessel n, wherein the dilution ratio represents the extent to which the mixture of the sample solution and the diluent has been diluted by the diluent mixed into vessel n. The dilution ratio may be calculated for any number of dilution steps of a dilution protocol across a volume range with the fourth dilution-related method of the present invention using the equation $$R'_{mn} = \frac{R_{0n}}{R_{0m}} \tag{1.1}$$

where ($R'_{mn}$) is the dilution ratio that has occurred as the mixture of sample solution and diluent is transferred from vessel m and mixed into the diluent in vessel n. This equation is a quotient of equation (0.9) expressed for the overall dilution from the source vessel, denoted by the subscript 0, to vessel n, and also equation (0.9) expressed for the overall dilution from the source vessel to vessel m, which directly precedes vessel n in the dilution protocol. A more useful form of equation (1.1) can be derived by substitution of the terms in equation (0.9) and algebraically simplifying to give:

$$R'_{mn} = \frac{a_{s'}}{a_s} \cdot \frac{A_{m,\lambda_s}}{A_{m,\lambda_d}} \cdot \frac{A_{n,\lambda_d}}{A_{n,\lambda_{s'}}} \tag{1.2}$$

where ($a_s$) is the absorbance per unit pathlength of the spectral feature s, unique to the sample solution, which results in a measurable absorbance in vessel m, ($a_{s'}$) is the absorbance per unit pathlength of the spectral feature s', also unique to the sample solution but different than spectral feature s, which results in a measurable absorbance in vessel n, $(A_{m,\lambda s})$ is the measured absorbance in vessel m at the wavelength $\lambda_s$ which corresponds to the spectral feature s of the sample solution, $(A_{m,\lambda d})$ is the measured absorbance in vessel m at the wavelength $\lambda_d$ which corresponds to the spectral feature that is common between the sample and diluent solutions, $(A_{n,\lambda d})$ is the measured absorbance in vessel n at the wavelength $\lambda_d$ which corresponds to the spectral feature that is common between the sample and diluent solutions, $(A_{n,\lambda s'})$ is the measured absorbance in vessel n at the wavelength $\lambda_{s'}$ which corresponds to the spectral feature s' of the sample solution.

By using a solution containing multiple dyes and multiple light absorbance spectral features, dilution ratios for all steps of a dilution scheme can be measured using equations (0.8), (0.9) and (1.2). Not all spectral features will be within the measurable absorbance range of the spectrophotometer. However, while one spectral feature may result in measurable absorbance values within the first few dilution steps, another spectral feature would provide measurable absorbance values only after multiple steps in the dilution scheme have already been made. Thus, if the dilution method is followed and different spectral features are used, the accuracy of each step can be determined.

The present invention may further be used to determine volume through features associated with a diluent as follows. A method of the invention for determining a liquid volume of a sample solution in a vessel, wherein the vessel includes a bottom and known dimensions, involves the steps of: a) adding to the vessel a diluent including a known concentration or concentrations of one or more diluent dyes, resulting in a diluent with multiple light absorbance spectral features at a corresponding number of distinct wavelengths; b) measuring absorbance at one or more of the distinct wavelengths; c) adding a volume of the sample solution to the vessel, wherein the sample solution has no measurable absorbance at the distinct wavelengths of the multiple light absorbance spectral features of the diluent; d) mixing the diluent and the sample solution in the vessel to produce a mixture of the sample solution and the diluent; e) measuring measurable absorbances of the mixture of the sample solution and the diluent; and f) calculating the volume of the sample solution added to the vessel based on the measured absorbances. In this method, the sample solution may contain no dye or one dye having one light absorbance spectral feature at a corresponding wavelength distinct from any wavelength of the distinct wavelengths of the multiple spectral features of the diluent. Alternatively, the sample solution may contain one or more dyes producing a plurality of light absorbance spectral features at corresponding distinct wavelengths. The distinct wavelengths of the light absorbance spectral features of the one or more dyes of the sample solution may all be different from the distinct wavelengths of the multiple spectral features of the diluent, or one of the distinct wavelengths of the light absorbance spectral features of the one or more dyes of the sample solution may be the same as one of the distinct wavelengths of the multiple spectral features of the diluent.

It is further to be noted that the present invention includes a system for testing or calibrating a liquid delivery volume comprising at least a portion of the following:

a photometric measurement means that measures optical absorbance at more than one wavelength and which is capable of communicating results to an external printer or computer, one or more sample solutions that are delivered by the device being tested, each sample solution containing one or more dyes, the combination of dyes providing two or more distinct detectable light absorbance spectral features, a known volume of diluent solution that contains no dye, but which may contain a buffer to maintain constant pH, provision for the sample solution and the diluent solution to be mixed, either automatically or manually, and computer executable firmware for calculating the volume of liquid dispensed by the dispenser being tested, based on the measurement of absorbance, the optical properties of the solutions, the dimensions of the vessel containing the mixture of sample and diluent solutions, and the volume of diluent.

It is further to be noted that the present invention includes a system for testing or calibrating liquid delivery volume comprising at least a portion of the following:

a photometric measurement means that measures optical absorbance at more than one wavelength and is capable of communicating results to an external printer or computer.

one or more sample solutions that are delivered by the device being tested, each sample solution containing one or more dyes, the combination of dyes providing two or more distinct detectable light absorbance spectral features, a diluent solution that contains one or more dyes and which may contain a buffer to maintain constant pH, provision for the sample solution and the diluent solution to be mixed, either automatically or manually, and computer executable firmware for calculating the volume of liquid dispensed by the dispenser being tested, based on the measurement of absorbance, the optical properties of the solutions, the dimensions of the vessel containing the mixture of sample and diluent solutions, and the volume of diluent.

Other variations of the examples and designs described and shown herein can be implemented. For example, and without intention to limit, a dilution mode algorithm may be included to calculate volume based on the dilution of a dye. Additionally, the processes, steps thereof and various examples and variations of these processes and steps, individually or in combination, may be implemented as a computer program product tangibly embodied as computer-readable signals on a computer-readable medium, for example, a non-volatile recording medium, an integrated circuit memory element, or a combination thereof. Such a computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual BASIC, XML, C, or C++, Fortran, Pascal, Eiffel, BASIC, COBOL, and the like, or any of a variety of combinations thereof.

It is to be understood that various modifications may be made to the apparatus, the method, and/or the kit as described herein without departing from the spirit and scope of the invention. For example, alternative dyes may be employed in a multi-dye solution. Accordingly, other embodiments are within the scope of the claims appended hereto.

What is claimed is:

1. A method of determining a liquid volume of a sample, the method comprising the steps of:
 a. providing in the sample a single solution including one or more dyes selected to produce in the sample multiple distinct detectable light absorbance spectral features, wherein the one or more dyes establish in the solution a first distinct detectable light absorbance spectral feature for a low volume or dilution range and a second distinct detectable light absorbance spectral feature for a high volume or dilution range;

b. measuring the light absorbance of multiple spectral features in the solution; and c. determining the volume of the sample from the measured light absorbance of the sample.

2. The method of claim 1 wherein the multiple distinct detectable light absorbance spectral features are selected for measurement where there is a valley or plateau resulting in a slope close to zero.

3. The method of claim 1 comprising the step of selecting for the solution a first dye and a second dye, wherein the first dye establishes in the solution the first distinct detectable light absorbance spectral feature for the low volume or dilution range and the second dye establishes the second distinct detectable light absorbance spectral feature for the high volume or dilution range.

4. The method of claim 3 wherein the first dye is at a concentration giving a high absorbance per unit pathlength in the solution and the second dye is at a concentration giving a low absorbance per unit pathlength in the solution.

5. The method of claim 1 comprising the step of selecting for the solution a first dye and a second dye, wherein the first dye establishes in the solution the first distinct detectable light absorbance spectral feature for the first volume or dilution range and the second distinct detectable light absorbance spectral feature for the second volume or dilution range, and the second dye establishes a third distinct detectable light absorbance spectral feature for a third volume or dilution range and a fourth distinct detectable light absorbance spectral feature for a fourth volume or dilution range.

6. The method of claim 1 comprising the step of selecting for the solution only one dye to establish in the solution the first distinct detectable light absorbance spectral feature for the low volume or dilution range and the second distinct detectable light absorbance spectral feature for the high volume or dilution range.

7. The method of claim 1 comprising the step of selecting for the solution a first dye, a second dye, a third dye and a fourth dye, wherein the first dye establishes in the solution the first distinct detectable light absorbance spectral feature for the low volume or dilution range, the second dye establishes in the solution the second distinct detectable light absorbance spectral feature for the high volume or dilution range, the third dye establishes in the solution a third distinct detectable light absorbance spectral feature for a third volume or dilution range, and the fourth dye establishes in the solution a fourth distinct detectable light absorbance spectral feature for a fourth volume or dilution range.

* * * * *